United States Patent [19]  [11] 4,008,241
Gelbein et al. [45] Feb. 15, 1977

[54] NICOTINAMIDE PRODUCTION

[75] Inventors: Abraham P. Gelbein, Plainfield; John E. Paustian, Whittany; Morgan C. Sze, Upper Montclair, all of N.J.

[73] Assignee: The Lummus Company, Bloomfield, N.J.

[22] Filed: Sept. 2, 1975

[21] Appl. No.: 609,626

[52] U.S. Cl. .................. 260/295.5 A; 260/295.5 R
[51] Int. Cl.$^2$ ..................................... C07D 213/56
[58] Field of Search ............. 260/295.5 A, 295.5 R

[56] References Cited
OTHER PUBLICATIONS

Krewson et al., Journal of the American Chemical Society, vol. 65 (11) pp. 2256–2257 (Nov. 1943).
Nikiforov et al., Chem. Abstracts, vol. 79 (21), 126, 259r, Nov. 26, 1973.

Primary Examiner—Alan L. Rotman
Attorney, Agent, or Firm—Marn & Jangarathis

[57] ABSTRACT

Nicotinamide is produced by aqueous ammonia hydrolysis of nicotinonitrile wherein the conversion is limited to at least 30% and no greater than 70%, with the nicotinonitrile concentration, expressed as weight product amide per 100 pounds of water, being at least 100 parts and no greater than 300 parts, with the hydrolysis being effected in the presence of ammonium nicotinate in an amount sufficient to essentially eliminate net production thereof. Ammonia and nicotinonitrile are stripped from the hydrolysis effluent, and nicotinamide recovered, by crystallization, from the stripped hydrolysis effluent.

9 Claims, 1 Drawing Figure

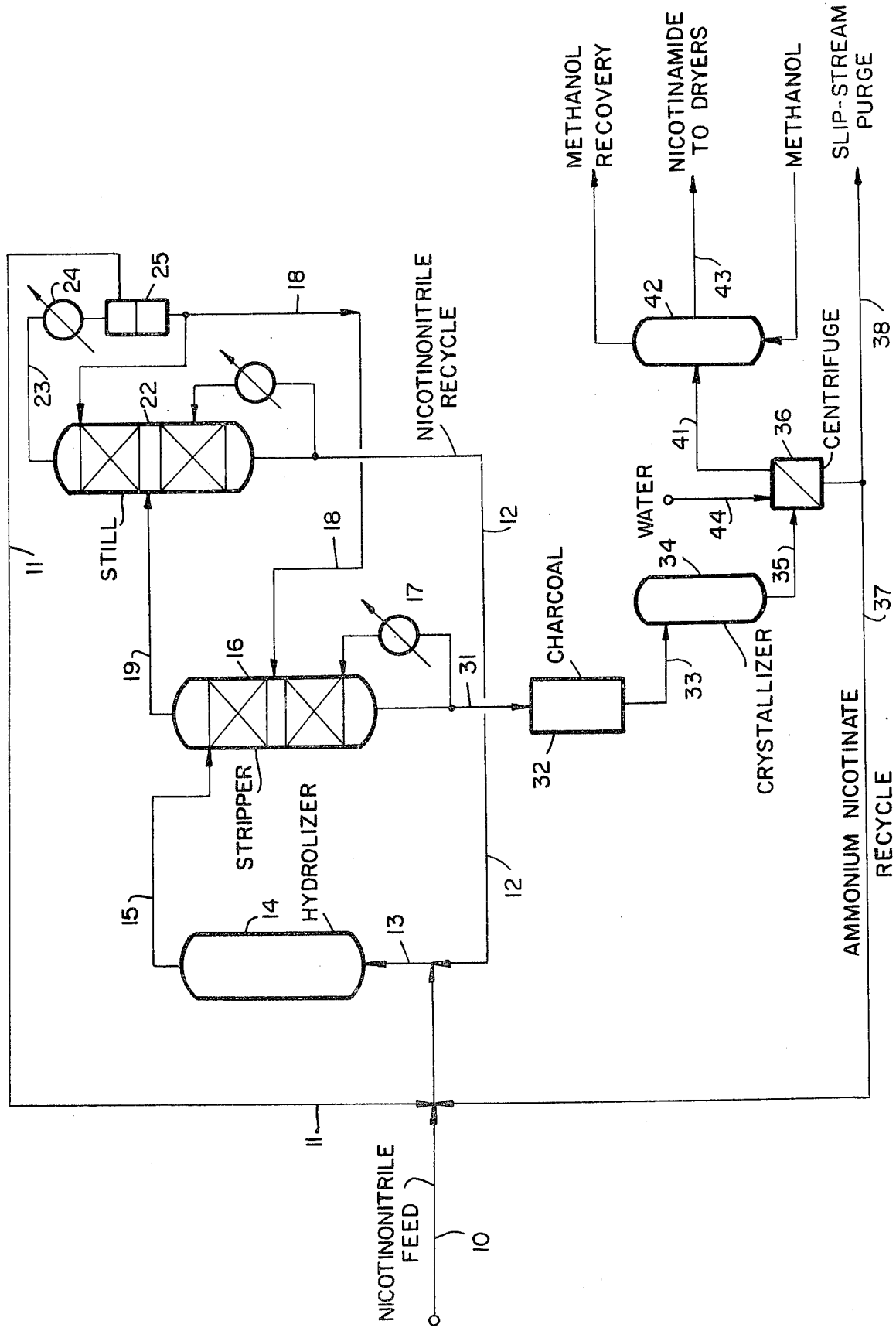

NICOTINAMIDE PRODUCTION

This invention relates to the production of nicotinamide, and more particularly to a new and improved process for producing nicotinamide from nicotinonitrile.

Nicotinamide is generally produced from nicotinonitrile by hydrolysis in the presence of sodium hydroxide. The production of nicotinamide from nicotinonitrile by sodium hydroxide hydrolysis has the disadvantage that the sodium hydroxide must be removed by neutralization and ion exchange. Accordingly, there is a need for a new and improved process for producing nicotinamide from nicotinonitrile.

An object of the present invention is to provide for the production of nicotinamide.

Another object of the present invention is to provide for the production of nicotinamide from nicotinonitrile by ammonia hydrolysis.

A further object of the present invention is to provide for the production of nicotinamide from nicotinonitrile by ammonia hydrolysis at high nicotinamide selectivity.

A still further object of the present invention is to provide a continuous process for producing nicotinamide from nicotinonitrile by ammonia hydrolysis.

These and other objects of the present invention will become more readily apparent from reading the following detailed descriptions thereof.

In accordance with the present invention, there is provided a process for producing nicotinamide from nicotinonitrile by ammonia hydrolysis of the nicotinonitrile in the presence of ammonium nicotinate with the hydrolysis being effected at a conversion of at least 30% and no greater than 70% in a solution having a nicotinonitrile concentration, expressed as weight product amide per 100 parts of water, of at least 100 parts, and no greater than 300 parts. The hydrolysis effluent is then stripped of ammonia and unreacted nicotinonitrile, followed by recovery of the nicotinamide from the stripped hydrolysis solution. Applicant has found that by effecting the ammonia hydrolysis at the hereinabove described conditions, it is possible to produce nicotinamide at an essentially 100% nicotinamide selectivity; i.e., without essential production of nicotinic acid or ammonium nicotinate, while simultaneously providing for economic recovery of the nicotinamide product.

More particularly, the ammonia hydrolysis of nicotinonitrile is effected in the presence of ammonium nicotinate, with the ammonium nicotinate being present in an amount which essentially eliminates net production thereof. In general, the ammonium nicotinate concentration is at least 6 parts per 100 parts of water, by weight, with the ammonium nicotinate preferably being provided by recycle of mother liquor from the nicotinamide recovery operation. The ammonia nicotinate is generally not employed in amounts in excess of about 10 parts per 100 parts of water; however, it is to be understood that greater amounts could be employed, but no economic benefit is obtained by the use of such greater amounts.

The nitrile conversion is controlled to at least 30%, and preferably at least 40%, and to no greater than 70%, and preferably no greater than 60%. The nitrile conversion is controlled to the hereinabove described conversions by coordinating the ammonia concentration with the time and temperature of hydrolysis. In general, the hydrolysis is effected at a temperature from 90° to 150° C, preferably from 100° to 125° C, at a time of from 4 to 8 hours, preferably from 5 to 7 hours, with the ammonia concentration generally being at least 3 molar, preferably at least 6 molar and generally no greater than 8 molar, preferably no greater than 7 molar. The proper coordination of time, temperature, and ammonia concentration to provide conversion, as hereinabove described, is deemed to be within the scope of those skilled in the art from the teachings herein. It is also to be understood that the nitrile conversion required to provide the high amide selectivity, as hereinabove described, can be effected without employing all of the temperatures, time, and ammonia concentrations hereinabove described, although such conditions are generally preferred.

The hydrolysis is effected at a nitrile concentration, expressed as weight product amide 100 parts of water, of at least 100 parts of amide, preferably at least 125 parts of amide, and no greater than 300 parts of amide, preferably no greater than 200 parts of amide. The hereinabove described nitrile concentrations, in combination with the conversion and presence of ammonium nicotinate permits essentially 100% selectivity to nicotinamide, while simultaneously permitting economic recovery of the final product.

Subsequent to the hydrolysis, unconverted nicotinonitrile and ammonia are separated from the hydrolysis effluent. The nicotinonitrile and ammonia are preferably recovered from the hydrolysis effluent by a stripping operation, with the stripping preferably being effected with an inert gas, such as steam. The stripping conditions are generally as follows: a temperature of from about 70° to about 150° C and a pressure from about 15 psia to about 140 psia. It is to be understood, however, that such conditions are only illustrative and the use of other conditions are deemed to be within the scope of those skilled in the art. In addition, the separation can be effected other than by a stripping operation.

Nicotinamide is then recovered from the stripped hydrolysis effluent, with such recovery preferably being effected by crystallization of the nicotinamide from the mother liquor. The crystallization is preferably effected by cooling the stripped hydrolysis effluent to a temperature of from about 30° to about 5° C, and preferably from about 15° to about 10° C. The crystallization is generally effected to recover from about 50 to about 95%, preferably from about 75 to 90% of the nicotinamide from the mother liquor. All or a portion of the mother liquor is then recycled to the hydrolysis operation in order to provide ammonium nicotinate for essentially eliminating net production thereof during the hydrolysis.

The invention will be further described with respect to an embodiment thereof illustrated in the accompanying drawing wherein:

The drawing is a simplified schematic flow diagram of an embodiment of the present invention for producing nicotinamide.

It is to be understood, however, that the scope of the present invention is not to be limited to the illustrative embodiment.

Referring now to the drawing, a feed comprised of nicotinonitrile in line 10 is combined with ammonia in line 11 and recycle streams 12 and 37, obtained as hereinafter described, and the combined streams, in line 13, introduced into a hydrolyzer 14, operated at a temperature and time, which in combination with the ammonia concentration in the feed, provides for a nicotinonitrile conversion within the hereinabove described limits. In addition, the total feed to the hydrolyzer 14 has a nicotinonitrile concentration, as hereinabove described.

A hydrolysis effluent is withdrawn from hydrolyzer 14 through line 15 and introduced into a stripping column 16 to recover, as bottoms, an aqueous solution of nicotinamide containing a small amount of ammonium nicotinate and unreacted nicotinonitrile and as overhead, unreacted nicotinonitrile, water and ammonia. The stripping requirement for the column 16 is provided by reboiling of steam generated in a reboiler generally designated at 17, with the concentration of product in line 31 controlled by refluxing a portion of the condensate recovered from the stripper overhead, introduced through line 18, and obtained as hereinafter described.

An overhead of nicotinonitrile, ammonia and water vapor is withdrawn from stripping column 16 through line 19 and sent to distillation column 22 to effect separation of the nicotinonitrile as an aqueous bottoms product and an overhead product containing water and ammonia.

The vapor, withdrawn from vessel 22 through line 23, is cooled in partial condenser 24 to a temperature to effect partial condensation of the overhead, with the condensate being recovered in vessel 25.

A portion of the condensate recovered in vessel 25 is returned to stripper 18 to control the concentration of the stripper bottoms product. The remaining portion of the condensate is used as reflux in still 22. The uncondensed portion of the vapor, is recycled to the hydrolyzer through line 11 to provide the ammonia requirements for the hydrolysis.

A bottoms stream comprised of an aqueous solution of nicotinamide, containing minor portions of ammonium nicotinate and nicotinonitrile, is withdrawn from stripper 16 through line 31 and passed through a column 32, containing a suitable adsorbent, such as charcoal, to effect decolorization thereof. The decolorized solution withdrawn from column 32 through line 33 is introduced into a crystallizer 34 to effect crystallization of nicotinamide. In general, the crystallizer is operated to effect cooling of the feed to a temperature of from 5° to 30° C, to effect crystallization of from 50 to 95% of the nicotinamide.

A slurry of nicotinamide crystals in mother liquor containing ammonium nicotinate and nicotinonitrile is withdrawn from crystallizer 34 through line 35 and introduced into a suitable separator, such as a centrifuge, schematically indicated as 36, to separate nicotinamide from mother liquor. Mother liquor withdrawn from centrifuge 36 through line 37 is recycled to hydrolyzer 14 through line 37 to provide the ammonium nicotinate requirements for the hydrolysis, which, as hereinabove described, essentially eliminates net production thereof. Another part is purged through line 38 to prevent buildup of impurities.

The nicotinamide crystals withdrawn from centrifuge 36 through line 41 is introduced into a washing zone, schematically indicated as 42, wherein the nicotinamide crystals are washed with methanol, with the nicotinamide product being recovered through line 43.

Methanol withdrawn from zone 42 can be recovered for re-use in zone 42.

The invention will be further described with respect to the following examples. It is to be understood, however, that the scope of the invention is not to be limited thereby.

EXAMPLE I

In one experiment, nicotinonitrile was hydrolyzed in 6 molar ammonia for 6 hours at 115° C and a nitrile concentration equivalent to 150 parts b.w. of product amide per 100 parts b.w. of water. Analysis of the reaction mixture by liquid chromatography showed a composition (neglecting water and ammonia) of 47.6 mole % nicotinonitrile, 49.8 mole % nicotinamide and 2.6 mole % nicotinic acid. This represents a nicotinonitrile conversion of 52.4 mole % with a selectivity to nicotinamide of 95.0 mole %.

EXAMPLE II

In another experiment conducted in a manner similar to that of Example I, 6.5 mole % ammonium nicotinate was added to the nicotinonitrile feed. The selectivity to nicotinamide was thereby increased to 100%.

EXAMPLE III

A material balance for the overall process is tabulated in Table I for a product rate of 100 moles/hr. nicotinamide. Hydrolyzer operating conditions are: temperature 115° C, pressure 60 psia, reaction time 6 hours. Resulting nicotinonitrile conversion is 46% and ammonia concentration 5.1 molar (based on water). Stripper 16 operating conditions are: temperature 100° C (approx.), pressure 15 psia (approx.), reboiler duty 14 lbs. steam/lb. nicotinamide product (approx.). The nicotinonitrile distillation column 22 is operated to produce a bottoms product (stream 12) containing approximately 50 wt. % nicotinonitrile. The overhead from this column (stream 23) is partially condensed at 43° C (110° F). The condensate (stream 18) is an 11 wt. % aqua ammonia solution, while the vapor (stream 11) contains 79 mole % ammonia and 21 mole % water.

After decolorization by passage through activated charcoal column 32, the stripper bottoms product is cooled to 10° C (50° F) in crystallizer 34. The resulting slurry is centrifuged and the cake washed with water. The amount of wash water used (stream 44) is equivalent to that consumed in the hydrolysis reaction (1 mole/mole amide product) plus that retained in the wet product cake. The resulting washed product is essentially pure nicotinamide (dry basis), corresponding to a nicotinamide recovery across the crystallization step of 81%. In addition to being saturated with nicotinamide, the mother liquor contains unreacted nicotinonitrile (4.4% of the nicotinonitrile charge to the hydrolyzer) and ammonium nicotinate (8.2 mole % of the total organic feed to the hydrolyzer). Conventional dehydration with methanol is used to finally dry the product nicotinamide.

TABLE I

EXAMPLE 3 MATERIAL BALANCE
BASIS: 100 MOLES/HR. NICOTINAMIDE

| Stream No. : Description | Nicotinonitrile | Nicotinamide | Nicotinic Acid | Water | Ammonia |
|---|---|---|---|---|---|
| 10: Feed Nicotinonitrile | 100.0 | | | | |
| 11: Condenser Vapor | | | | 26.0 | 95.9 |
| 12: Still Bottom | 107.9 | | | 697.4 | |
| 13: Hydrolyzer Feed | 217.5 | 23.0 | 21.6 | 1287.5 | 117.5 |
| 15: Hydrolyzer Product | 117.5 | 123.0 | 21.6 | 1187.5 | 117.5 |
| 18: Condenser Liquid | | | | 8709.6 | 1155.1 |
| 19: Stripper Top | 107.9 | | | 9433.0 | 1251.0 |
| 31: Stripper Bottoms | 9.56 | 123.0 | 21.6 | 464.1 | 21.6 |
| 37: Centrifuge Mother Liquor | 9.56 | 23.0 | 21.6 | 564.1 | 21.6 |
| 41: Centrifuge Amide Product | | 100.0 | | 100.0 | |
| 44: Centrifuge Wash Water | | | | 200.0 | |

The present invention is particularly advantageous in that nicotinamide can be produced by hydrolysis of nicotinonitrile, without the use of sodium hydroxide. Moreover, by proceeding in accordance with the present invention, it is possible to hydrolyze nicotinonitrile to nicotinamide, by the use of ammonia, at an essentially 100% nicotinamide selectivity, while simultaneously providing for economic recovery of the nicotinamide from the resulting hydrolysis effluent. Furthermore, nicotinamide can be produced from nicotinonitrile by a continuous operation.

Numerous modifications and variations of the present invention are possible in light of the above teachings and therefore, it is to be understood that within the scope of the appended claims, the invention may be practiced otherwise than as particularly described.

What is claimed is:

1. A continuous process for producing nicotinamide, at essentially 100% nicotinamide selectivity, comprising:
    a. hydrolyzing nicotinonitrile in an aqueous ammonia solution, said hydrolysis being effected at a nicotinonitrile concentration, expressed as parts by weight of product amide per 100 parts of water, of at least 100 parts and no greater than 300 parts, said hydrolysis being effected at a nicotinonitrile conversion of at least 30% and no greater than 70%, said hydrolysis being effected in the presence of ammonium nicotinate in an amount sufficient to essentially eliminate net production thereof to produce a hydrolysis effluent containing nicotinamide, ammonia, unconverted nicotinonitrile and ammonium nicotinate at a nicotinamide selectivity of essentially 100%;
    b. separating unconverted nicotinonitrile and ammonia from the hydrolysis effluent;
    c. recovering nicotinamide from the hydrolysis effluent to produce solid nicotinamide and a mother liquor containing nicotinamide and ammonium nicotinate; and
    d. recycling at least a portion of the mother liquor to the hydrolysis of step (a) in order to provide ammonium nicotinate.

2. The process of claim 1 wherein said hydrolysis is effected at a temperature of from about 90° to about 150° C, a reaction time of from 4 to 8 hours, and at an ammonia concentration of from 3 to 8 molar.

3. The process of claim 2 wherein the hydrolysis is effected in the presence of at least 6 parts of ammonium nicotinate per 100 parts of water.

4. The process of claim 3 wherein the conversion of nicotinonitrile is at least 40% and no greater than 60%.

5. The process of claim 4 wherein the temperature is from 100° to 125° C, the time from 5 to 7 hours and the ammonia concentration at least 6 molar and no greater than 7 molar.

6. The process of claim 3 wherein nicotinamide is recovered from the hydrolysis effluent by partial crystallization.

7. The process of claim 6 wherein the crystallization is effected at a temperature of from 5° to 30° C to recover from 50 to 95% of the nicotinamide from the mother liquor.

8. The process of claim 6 wherein nicotinonitrile and ammonia recovered from the hydrolysis effluent are recycled to the hydrolysis.

9. The process of claim 1 wherein unconverted nicotinonitrile and ammonia are separated from the hydrolysis effluent by stripping nicotinonitrile, ammonia and water, as a gas, from the hydrolysis effluent;
    distilling the gas to recover an ammonia and water overhead and an aqueous nicotinonitrile bottoms;
    recycling the aqueous nicotinonitrile bottoms to step (a);
    condensing a portion of the overhead and recycling the condensed portion to the stripping; and
    recycling the uncondensed portion of the overhead to step (a).

* * * * *